United States Patent
Manning (10) Patent No.: US 6,178,822 B1
(45) Date of Patent: *Jan. 30, 2001

(54) METHOD AND DEVICE FOR MULTIPLEXED SPECTRO-RHEOLOGICAL MEASUREMENTS

(76) Inventor: Christopher J. Manning, 502 S. Blaine St., Moscow, ID (US) 83840

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/974,385

(22) Filed: Nov. 19, 1997

Related U.S. Application Data (60) Provisional application No. 60/031,179, filed on Nov. 19, 1996, and provisional application No. 60/054,786, filed on Aug. 5, 1997.

(51) Int. Cl.[7] .................................................. G01N 3/32

(52) U.S. Cl. ................................. 73/668; 73/579; 250/339

(58) Field of Search .................................. 73/822, 54.24, 73/574, 579, 763, 662, 663, 665, 667, 668; 250/339; 356/346

(56) References Cited

U.S. PATENT DOCUMENTS

| | | | |
|---|---|---|---|
| 4,181,029 | * 1/1980 | Talbot, Jr. ............................. | 73/665 |
| 4,418,573 | * 12/1983 | Madigosky et al. ................... | 73/574 |
| 4,537,076 | * 8/1985 | Lax et al. .............................. | 73/662 |
| 5,113,353 | * 5/1992 | George ................................. | 73/54.24 |
| 5,245,876 | * 9/1993 | Jones ..................................... | 73/579 |
| 5,269,190 | 12/1993 | Kramer et al. . | |
| 5,345,825 | * 9/1994 | Lee et al. .............................. | 73/574 |
| 5,450,196 | * 9/1995 | Turner .................................. | 356/346 |
| 5,750,884 | * 5/1998 | Field ..................................... | 73/54.24 |

OTHER PUBLICATIONS

Christopher J. Manning and Peter R. Griffiths, Multiple–modulation double–Fourier transform IR spectrometry, SPIE, vol. 2089, (1993) pp. 248–249.

Paul Horowitz and Winfield Hill, *The Art of Electronics*, Cambridge University Press, (1980), pp. 437–442.

Volker Abetz, Gerald G. Fuller, and Reimund Stadler, Infrared Linear Dichroism Spectroscopy by a Double Modulation Technique, Polymer Bulletin 23, (1990) pp. 447–454.

Isao Noda, A. E. Dowrey, and Curtis Marcott, Modulation Spectroscopy, SPIE vol. 553 1985 Fourier and Computerized Infrared Spectroscopy (1985) pp. 56–62.

Isao Noda, A. E. Dowrey, and Curtis Marcott, A Spectrometer for Measuring Time–Resolved Infrared Linear Dichroism Induced by a Small–Amplitude Oscillatory Strain, vol. 42, No. 2, 1988, Applied Spectroscopy, pp. 203–216.

Boiana O. Budevska, Christopher J. Manning, Peter R. Griffiths and Robert T. Roginski, Step–Scan Fourier Transform Infrared Study on the Effect of Dynamic Strain on Isotactic Polypropylene,vol. 47, No. 11, 1993, Applied Spectroscopy, pp. 1843–1851.

Isoa Noda, Two–Dimensional Infrared (2D IR) Spectroscopy: Theory and Applications, vol. 44, No. 4, 1990, Applied Spectroscopy, pp. 550–561.

(List continued on next page.)

*Primary Examiner*—Max Noori
(74) *Attorney, Agent, or Firm*—Antton & Associates P.C.

(57) ABSTRACT

Three or more frequency components are used as deformation waveforms to perturb a sample during spectroscopic measurement. Simultaneously measuring more than one frequency allows for multiplexing. Further, many frequencies insure that the optimal perturbation frequencies for a particular measurement are present. The multiplex advantage of a particular spectroscopic instrument may accrue simultaneously with a multiplex advantage in the characterization of the time dependence of the sample response.

12 Claims, 7 Drawing Sheets

OTHER PUBLICATIONS

Richard A. Palmer, Christopher J. Manning, James L. Chao, Isao Noda, Anthony E. Dowrey, and Curtis Marcott, Application of Step–Scan Interferometry to Two–Dimensional Fourier Transform Infrared (2D FT–IR) Correlation Spectroscopy, vol. 45, No. 1, 1991, Applied Spectroscopy, pp. 12–17.

J. A. Graham, W. M. Grim, III, and W. G. Fateley, Studies of Polymers by Stroboscpic FT–IR, Journal of Molecular Structure, 113 (1984) pp. 311–322.

I. Noda, S. D. Smith, A. E. Dowrey, J. T. Grothaus, and C. Marcott, Dynamic IR Studies of Microdomain Interphases of Isotope–Labeled Block Copolymers, Presented at the Fall meeting of the Materials Research Society Boston, 1989, (Abstract).

Isao Noda, *Two–Dimensional Infrared Spectroscopy*, J. Am Chem. Soc. 1989, vol. 111, pp. 8116–8118.

C. J. Manning, G. L. Pariente, B. D. Lerner, J. H. Perkins, R. S. Jackson and P. R. Griffiths, Multiple Modulation Step–Scanning Fourier Transform Infrared Spectroscopy, Computer Assisted Analytical Spectroscopy, John Wiley & Sons, 1996, pp. 1–23.

Isao Noda, *Two–Dimensional Infrared (2D IR) Spectroscopy*, the Mar. meeting of the American Physical Society: Las Vegas, Nevada, Apr. 2, 1986; Abstract HWb–29.

I. Noda, A. E. Dowrey and C. Marcott, *Submolecular Interactions of Polymers Studied by Two–Dimensional Infrared (2D IR) Spectroscopy*, the Mar. meeting of the American Physical Society: New Orleans, Louisiana, Mar. 23, 1988, Abstract K25b–3.

Isao Noda, A. E. Dowrey and Curtis Marcott, Dynamic Infrared Linear Dichroism (DIRLD) and Two–Dimensional Infrared (2D IR) Analysis of Polymers, IUPAC $32^{nd}$ International Symposium of Macromolecules: Kyoto, Japan, Aug. 3, 1988; Abstract 3–6–16.

Stephan Stinson, Two–Dimensional IR Spectroscopy may Simplify Complex Spectra, C&EN, Jan. 1, 1990, pp. 21–24.

Manning Applied Technology, *Polymer Modulator*, 1997 (Brochure).

Boiana O. Budevska, Christopher J. Manning and Peter R. Griffiths, Comparison of Two–Dimensional Power and Phase Spectra Generated from Sample Modulation Step––Scan FT–IR Experiments, vol. 48, No. 12, 1994, Applied Spectroscopy, pp. 1556–1559.

Christopher J. Manning, University Microfilms, 1991, Duke University, pp. 38–46: 78–81 and 122–128 (Excerpts from Dissertation).

* cited by examiner

METHOD AND DEVICE FOR MULTIPLEXED SPECTRO-RHEOLOGICAL MEASUREMENTS

RELATED APPLICATIONS

This application claims the benefit of Provisional Application Ser. No. 60/031,179 filed Nov. 19, 1996, and Ser. No. 60/054,786, filed on Aug. 5, 1997, both of which are incorporated herein by reference.

BACKGROUND AND SUMMARY OF THE INVENTION

The use of rheological, viscoelastic and dynamic-mechanical measurements to determine the macroscopic properties of materials is a well known art. Several commercially available instruments can make these types of measurements. Kramer et al, incorporated herein by reference, discloses an example of such instruments in U.S. Pat. No. 5,269,190. Kramer discloses variations on the use of a mechanical frame together with transducers for generating mechanical displacement, measuring mechanical displacement, and for measuring force. Ramp functions, in which strain or shear varies as a linear function of time, can be used. Force, as a function of time, may be measured after a sudden change of strain or shear. A manually operated eccentric for the purpose of generating a sudden change in shear or strain is disclosed by Kramer. In both of these cases, and in much of the practice of rheology, such forces can be applied to a sample once while the resulting force as a function of time is recorded. However, these forces are not modulated as a continuous functions of time. The technique of dynamic mechanical analysis does use single-frequency, continuous sinusoidal modulation in the measurement of loss angle as a function of frequency.

Spectroscopic measurements of submolecular components during sample deformation has been called spectro-rheology [R. A. Palmer, C. J. Manning, J. L. Chao, I. Noda, A. E. Dowrey, and C. Marcott, Appl. Spectrosc. 45, 12 (1991), "Application of Step-Scan Interferometry to Two-Dimensional Fourier Transform Infrared (2D FT-IR) Correlation Spectroscopy" and references therein.] However, there has been no use of continuous multifrequency waveforms in such measurements. Instead, single-frequency waveforms have been used almost exclusively. Continuous single-frequency sinusoidal deformation waveforms can be applied to samples to obtain spectroscopic measurements of samples undergoing deformation [see Palmer, et al.] Optical or spectroscopic measurements, particularly of the polarized infrared absorption or polarized Raman scattering of samples, may be used to obtain information about the time dependence of reorientation of the individual submolecular components. The origin of macroscopic rheological properties is the microscopic reorientation of the various submolecular components of a material. Hence, the use of spectroscopic measurements together with various deformation waveforms has the potential to provide deeper insight into the properties of materials.

To date, predominantly two types of deformations have been used in such spectro-rheological measurements. The first is to ramp strain as a single event in which the strain is increased linearly as a function of time. This approach closely follows the art of rheology and has the advantage that it can be used to study samples undergoing very large deformations which are inherently irreversible, i.e., the sample is irreversibly altered. A significant disadvantage of this approach is that it can be done only once with any particular sample. It is usually restricted to slow events because the signal-to-noise ratio (SNR) of measurements made by infrared, Raman and many other spectroscopic techniques is generally too low to observe rapid transients from a single event. The second common approach to spectro-rheological measurements has been to apply a continuously varying, sinusoidal strain having a small amplitude. This technique follows the art of dynamic mechanical analysis. Continuous signals modulate the spectroscopic properties of the sample. This approach has the advantage that the deformation cycle may be repeated many times so that signal averaging may then be used to improve the SNR of the resulting small spectral variations. The effective time resolution may also be greatly increased by such signal averaging. The principal disadvantage of this approach is that the signal amplitude is intrinsically limited by the requirement that the sample not be irreversibly altered by the deformation cycle.

Many of the advantages of rheo-optical spectroscopy have been discussed by Noda [see for example, I. Noda, Appl. Spectrosc. 44, 550 (1990), "Two-Dimensional Infrared (2D IR) Spectroscopy: Theory and Applications".] The general method allows the measurement of the reorientation of submolecular components of a polymer or other sample material. It can simplify interpretation of the spectrum of a material by reducing the portion giving a signature to only those which respond to a particular external perturbation, and further simplifies interpretation by the fact that, in general, each portion of a molecule which does respond to the perturbation does so with a different time delay. Typically the different submolecular groups (not to be confused with the monomer units) of a polymer or other material have differing vibrational absorption frequencies which can be independently monitored with an infrared, Raman or other spectrometer. Hence, the reorientation during or following mechanical perturbation can be observed separately for each subgroup at an appropriate wavelength or energy. Traditionally, these measurements have been made by the use of a single-frequency sinusoidal mechanical perturbation of the sample under study. It is possible, however, to gain advantage in signal-to-noise ratio and/or reduction of measurement time by the use of a multifrequency mechanical perturbation as disclosed herein.

Two simultaneously applied sinusoidal components have been used as a deformation force for spectro-rheology [C. J. Manning and P. R. Griffiths, 9th International Conference on Fourier Transform Spectroscopy, August, 1993, (*SPIE Proceedings*, Vol. 2089), 248 (1993)]. This approach has the advantage that the frequencies of the two components may be independently optimized for the purpose of obtaining information about particular submolecular motions. However, this approach does not automatically accomplish the necessary optimization of spectral components.

The present invention uses more than two, and preferably many more, frequency components in a deformation waveform. In general, submolecular motions have different time-scales for which different deformation frequencies are appropriate for probing. It is a feature of the present invention to provide a way to stress a sample simultaneously at more than one frequency. Measuring more than one frequency simultaneously can produce a multiplex advantage. It is possible to gain considerable advantage in signal-to-noise ratio and/or reduction of measurement time by the use of a multifrequency mechanical perturbation. The advantage is equal to square root of n, where n is the number of perturbation frequencies used simultaneously. Further, by using many frequencies the optimal frequencies may be included in the waveform. This multiplex advantage can complement the very different multiplex advantage arising in the spectroscopic portion of the measurement. The multiplex advantage of a particular spectroscopic instrument may accrue simultaneously with a multiplex advantage in the characterization of the time dependence of the sample response. Two extreme cases of the multifrequency waveform are suggested. One is a pulse waveform containing all frequencies within the bandwidth of the pulse generating equipment. In this case, the component frequencies of the pulse have the same phase, hence adding together in the time-domain to produce a large excursion in amplitude. Such pulses are readily generated by electrical means. The second extreme case also uses all frequencies within the bandwidth of the pulse generating equipment, but such that each component has random phase. In this case, the components do not add coherently at any point in the time domain. Hence, the dynamic range of the waveform applied to the sample is smaller, allowing more optimal use of the mechanical range of motion of the modulation device, but slightly complicating the measured data.

It is accordingly an objective of the present invention to measure the reorientation rates of submolecular components, particularly of polymeric materials, using a spectrometer together with the method and device described. It is also an objective of the present invention to use mechanical perturbation to simplify spectral interpretation. It is also an objective of the present invention to increase the signal-to-noise ratio of such measurements by using a multiplex advantage.

The foregoing objects, features and advantages of the present invention, and others also, are illustrated below with the aid of the attached figures.

DETAILED DESCRIPTION

Figure 1:
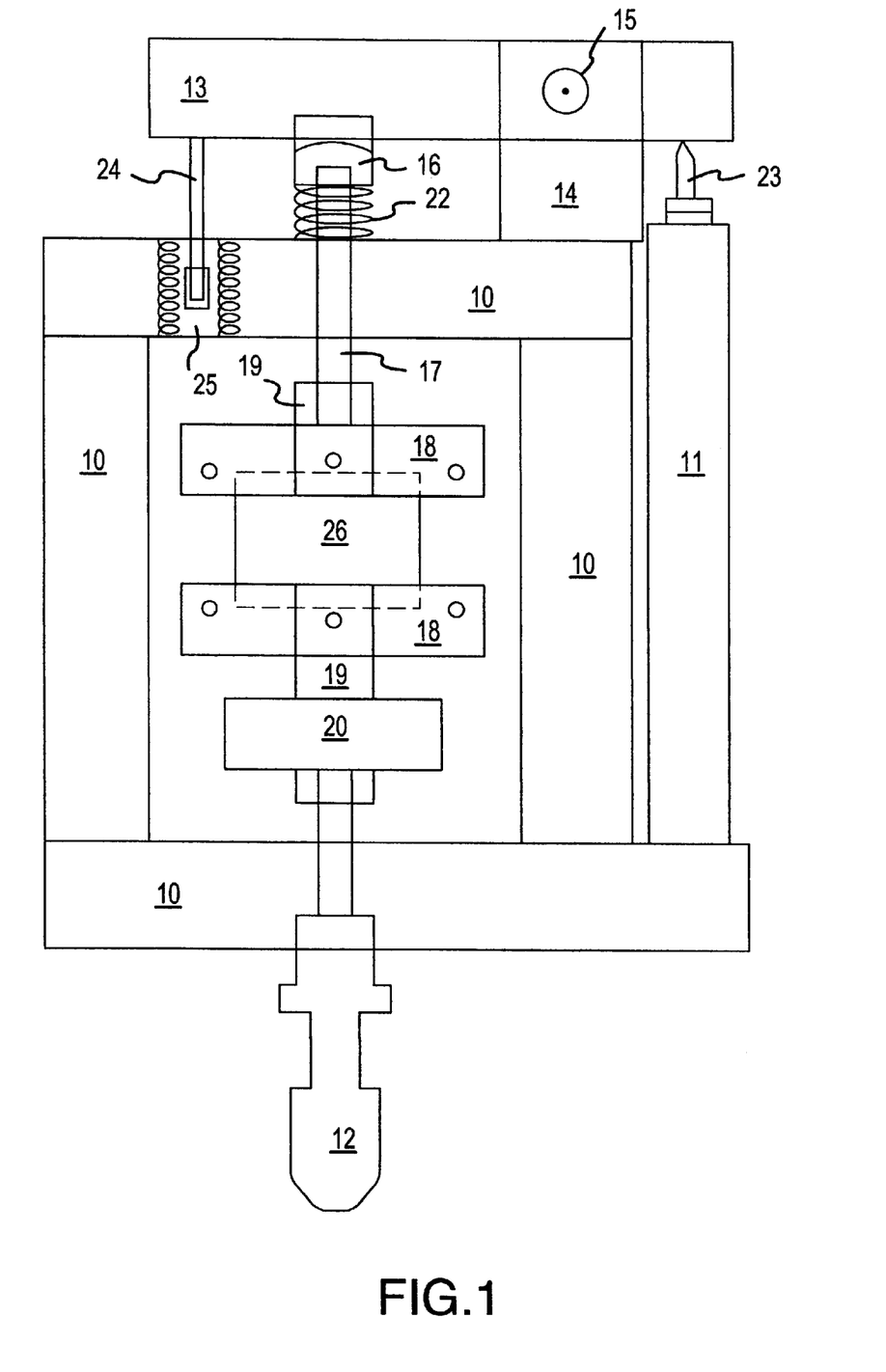
FIG. 1 is a diagram of one preferred embodiment of the device for deforming samples.

FIG. 1 is a diagram of a device suitable for generating and applying many different deformation waveforms to samples in a variety of sample mounting geometries. The device consists of frame members 10 which provide a rigid mount for the other components, including the piezoelectric or other transducer 11 which, via pushrod 23, actuates a force transfer device such as lever 13. The use of a lever is not an essential feature of the invention, but does allow amplification of the motion produced by a transducer. Lever 13 pivots on a pin or other suitable low-friction or frictionless rotating device or hinge 15 such that the pushrod 17 moves up and down according to the output of the transducer 11 so as to impart a change in force to the sample. The lever 13 is coupled to pushrod 17 by an adapter 16 which is spring-loaded by spring 22 against the lever 13. The combination of the spring 22 and transducer 11 insures that a sample 26 can experience a deformation force, such as tensile, stress, strain and/or shearing force, so that the sample can be both stretched and relaxed. The position of the lever 13 may be monitored by a suitable position transducer 25, which may be coupled to the lever 13 by a rod 24.

A sample 26 is mounted in the sample holders 18. A variety of sample mounting methods may be used which will result in different deformations being applied to the sample. The static tension, shear or pressure of the sample may be set by adjusting micrometer 12 and monitoring the output of force transducer 20. The sample holders 18 are mounted to adapters 19 which connect to the force transducer 20 and pushrod 17. The sample holders 18 provide a means for clamping the sample 26 such that it can be deformed. The tension in the sample 26 may be modulated by varying the voltage applied to the transducer 11. Various waveforms, described below, may be generated by any of the many means known in the art. It may be necessary to compensate the voltage, i.e., modify the waveform, applied to the transducer 11 to account for hysteresis and non-linearity. The device may be readily outfitted to allow the temperature of the sample to be controlled, e.g., by a flow of thermostatted gas.

Figure 2A:
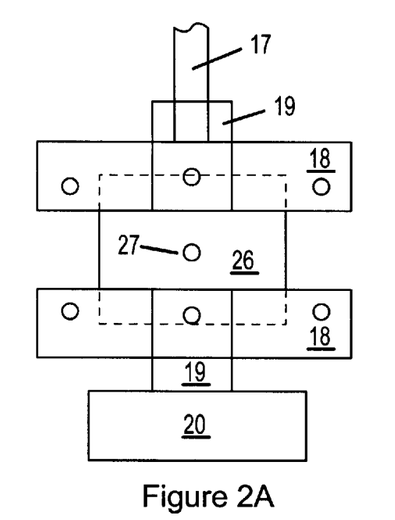
FIG. 2 is a diagram showing variations of the sample mounting components.
Figure 2B:
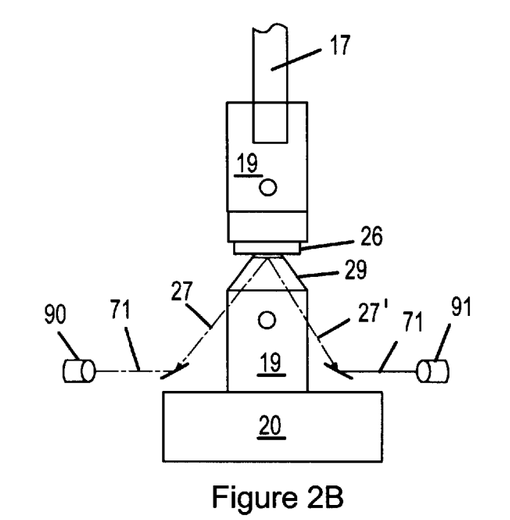

FIG. 2 shows several embodiments of the sample holders generally indicated by 18 in FIG. 1. FIG. 2A shows sample holders 18 suitable for clamping a thin film sample. Such sample holders would normally be used to modulate the strain of the sample in the axial direction. The path of radiation through the sample 26 is generally indicated by 27. FIG. 2B shows a attenuated total reflectance geometry suitable for modulating the pressure of a sample 26. A transparent window or crystal 29 allows radiation 71 from a source of radiant energy 70 to follow the path indicated by 27 so as to interact with the sample 26 and then to exit via path 27' to a detector 80. The source 70 and detector 80 can be components of a spectrometer. Suitable spectrometers are known in the art and generally include FT-IR spectrometers that work in infrared regions. Other suitable spectrometers include ultraviolet (UV) spectrometers, visible light spectrometers, fluorescent spectrometers and Raman spectrometers.

In the configuration of FIG. 2B the sample is compressed against the adapter 19 according to the static adjustment of the micrometer 12 of FIG. 1.

Figure 2C:
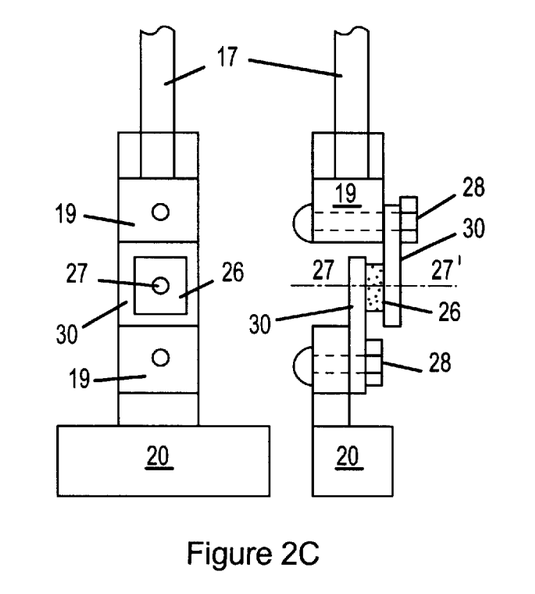

FIG. 2C discloses the use of two windows 30 that are transparent to the radiation of interest to sandwich a sample 26 such that the axial shear may be modulated. The windows 30 are fastened to adapters 19 by screws 28. Equivalent means for mounting the windows 30 include adhesives and clamps.

Again, the path of radiation 90 through the sample 26 is indicated by arrows 27 and 27'.

Figure 3:
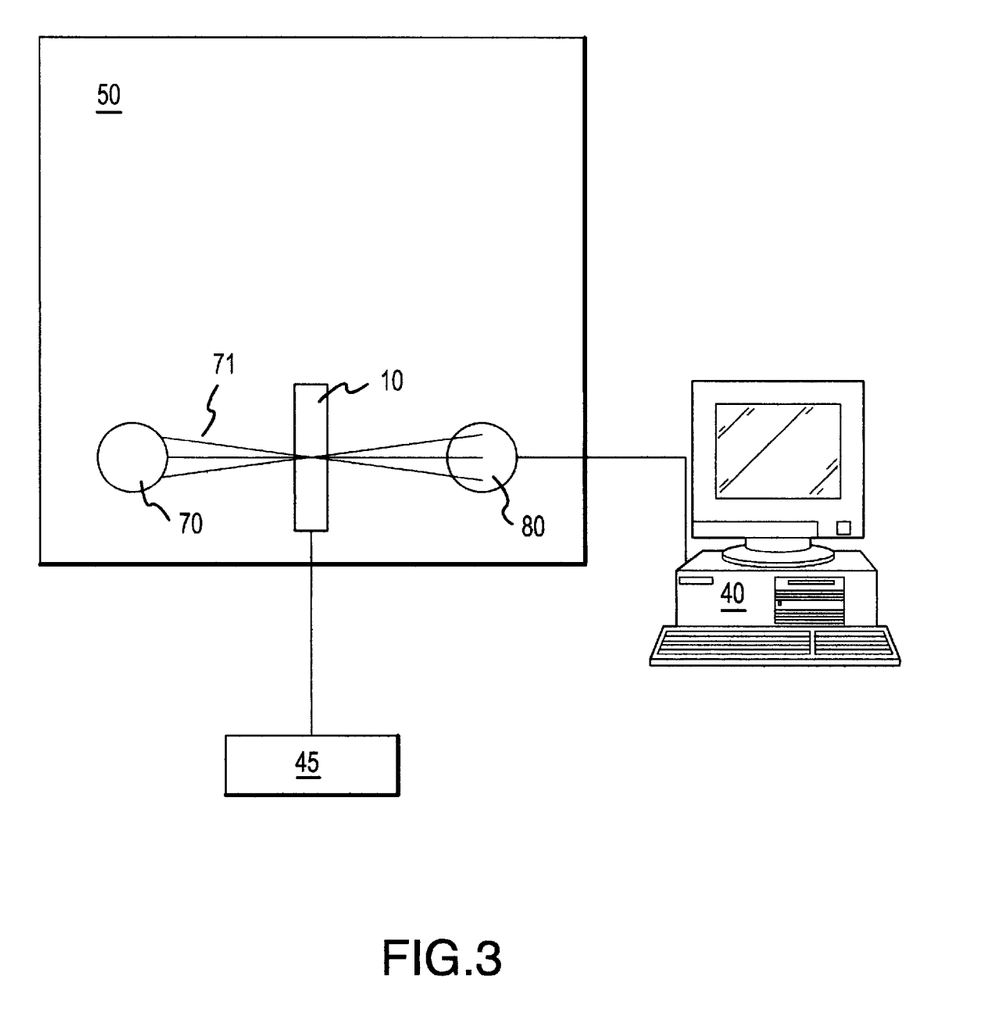
FIG. 3 is a diagram of one preferred use of the device for making spectroscopic measurements.

With a sample mounted in the device, the static tension, shear or pressure may be set by a micrometer 12. FIG. 3 shows the device, generally indicated by 10, of FIG. 1, mounted in a sample compartment of a spectrometer 50 so that a probe beam 71 generated by a source in the spectrometer 50 may interact with the sample. A suitable location external to the spectrometer may be equivalent, such external accessory mountings being well known in the art and include micro-sample accessories, microscopes, etc., in addition to the attenuated total reflectance and transmission geometries shown. Other optical components can be used to enhance the spectroscopic measurements, including photoelastic modulators, filters and polarizers. The demodulation may include either or both lock-in amplifiers and digital signal processing (examples of all of which are well known in the art). A waveform is applied to the transducer 11 to modulate the sample deformation. The spectral characteristics of the sample as a function of time are recorded from a detector 80 by the spectrometer data system 40, in synchronization to the waveform applied via electronic power unit 45. After the completion of data collection and demodulation the data may be analyzed by a variety of methods.

Figure 4:
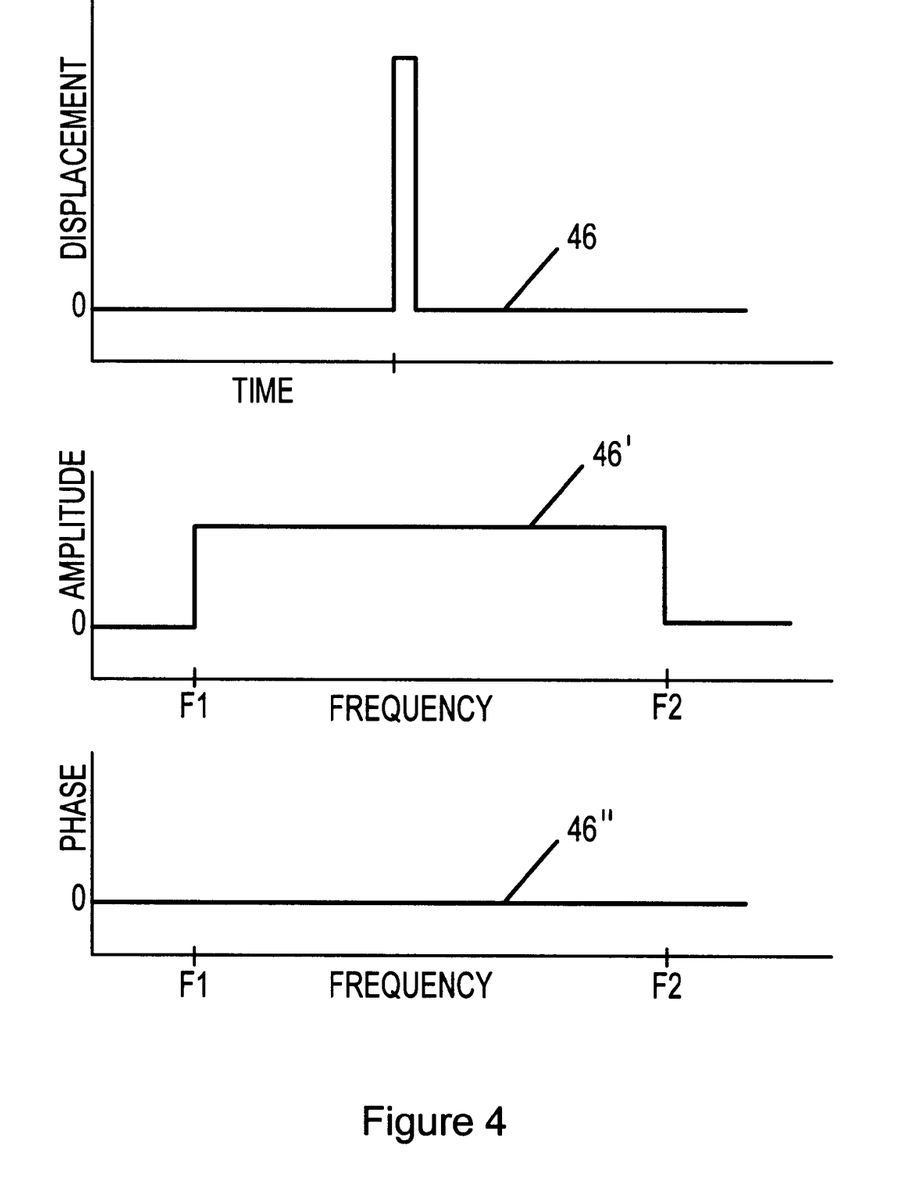
FIG. 4 is a diagram of one preferred waveform which may be applied to a sample.

FIG. 4 shows a diagram of one example of a multifrequency waveform. A pulse waveform 46 contains all frequencies within the bandwidth of the pulse generating equipment. The time domain representation of this signal is indicated by 46. The Fourier transform of this signal, indicated by 46', has essentially equal energy across a particular bandwidth of frequency between f1 and f2. The phase of the components in the frequency domain is indicated by 46". In this case, the component frequencies of the pulse have the same phase, hence adding the components together in the time-domain to produce the large excursion in amplitude of 46. Such pulses are readily generated by electrical means that are well known in the art.

Figure 5:
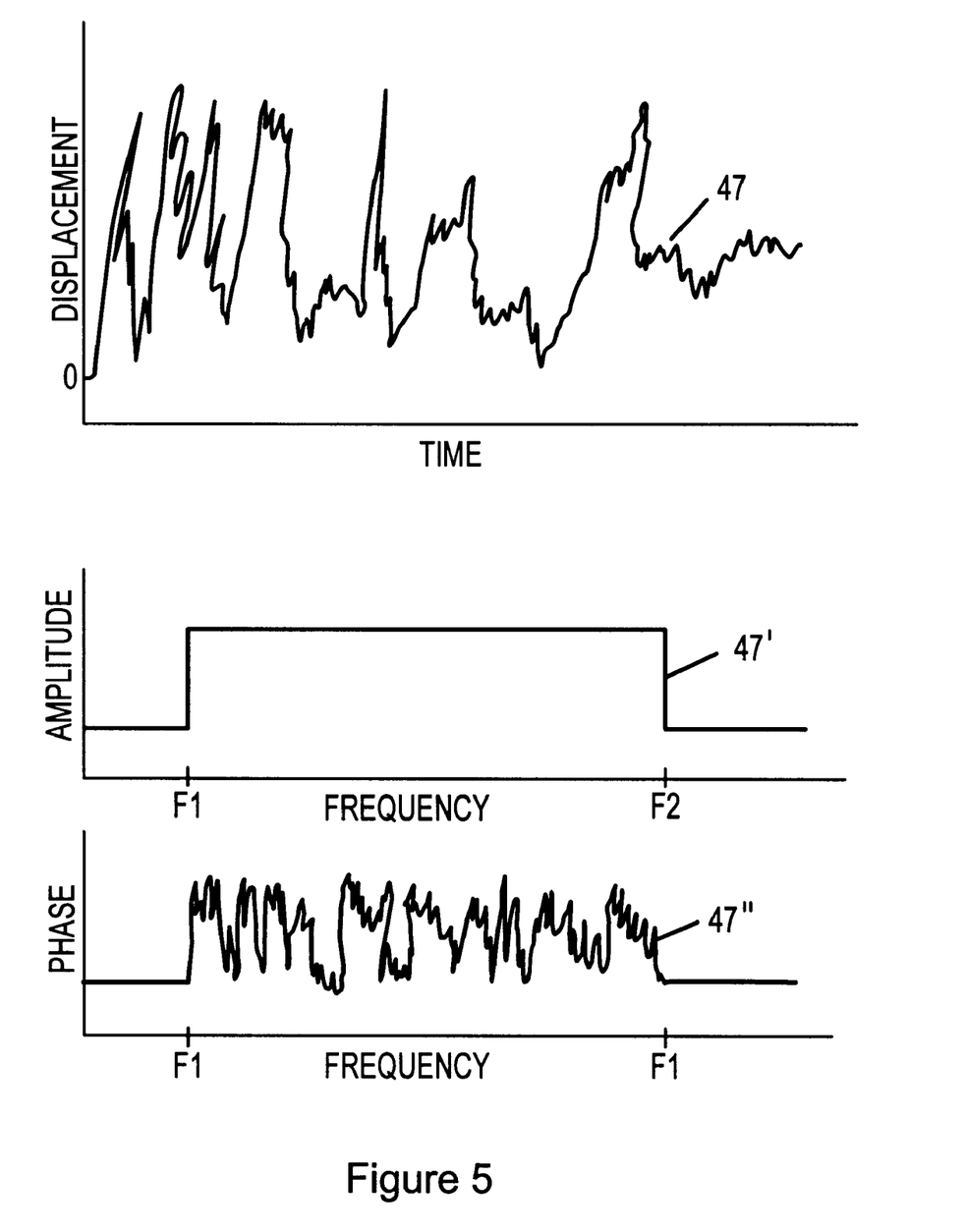
FIG. 5 is a diagram of a second preferred waveform which may be applied to a sample.

FIG. 5 shows another waveform embodiment that uses all frequencies within the bandwidth of the pulse generating equipment. However, each component in this embodiment has random phase. The time domain signal, indicated by 47, has a random structure because the component frequencies add randomly at each point in the time domain. The Fourier transform of this signal, indicated by 47', again has essentially constant energy across the bandwidth defined by f1 and f2. In this case, all of the components do not add coherently at any point in the time domain as because of the random phase indicated by 47". Hence, the dynamic range of the waveform applied to the sample is smaller, allowing more optimal use of the mechanical range of motion of the transducer. The generation of suitable waveforms is straightforward using, for example, a convenient source of random phase signals such as the well-known maximal length pseudorandom sequence generated from a shift register [Paul Horowitz and Winfield Hill, The Art of Electronics, (Cambridge: Cambridge University Press, 1980), p. 437–442.] Other sources of suitable signals include a variety of noise generation means that are well-known in the art.

Figure 6A:
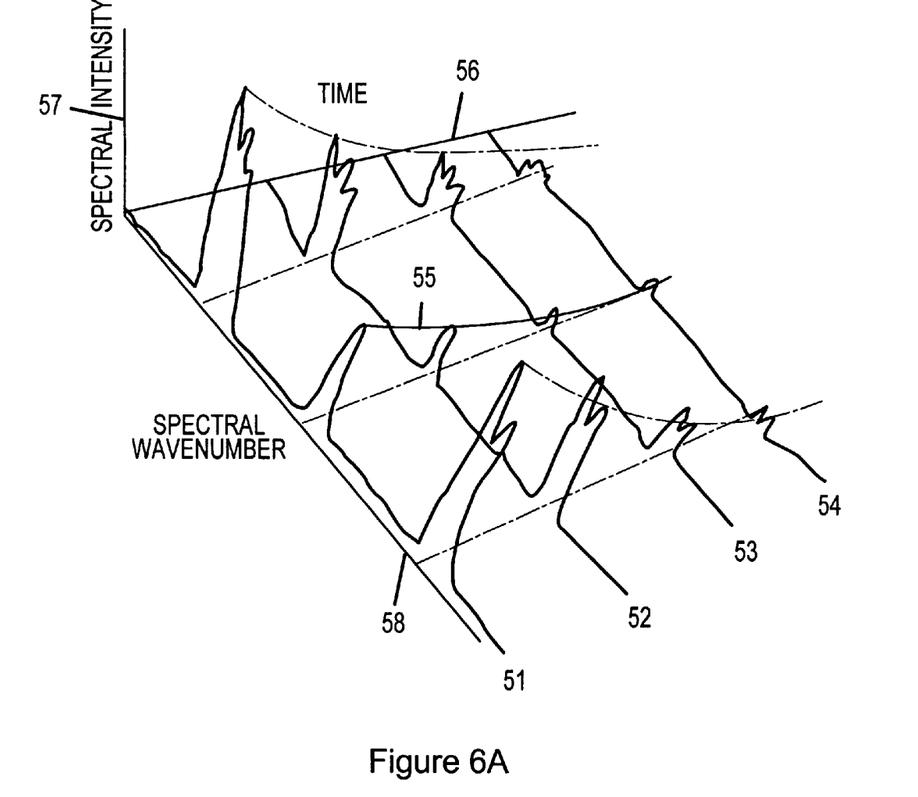
FIG. 6 is a diagram of one preferred method of analyzing and presenting data in the time domain.
Figure 6B:
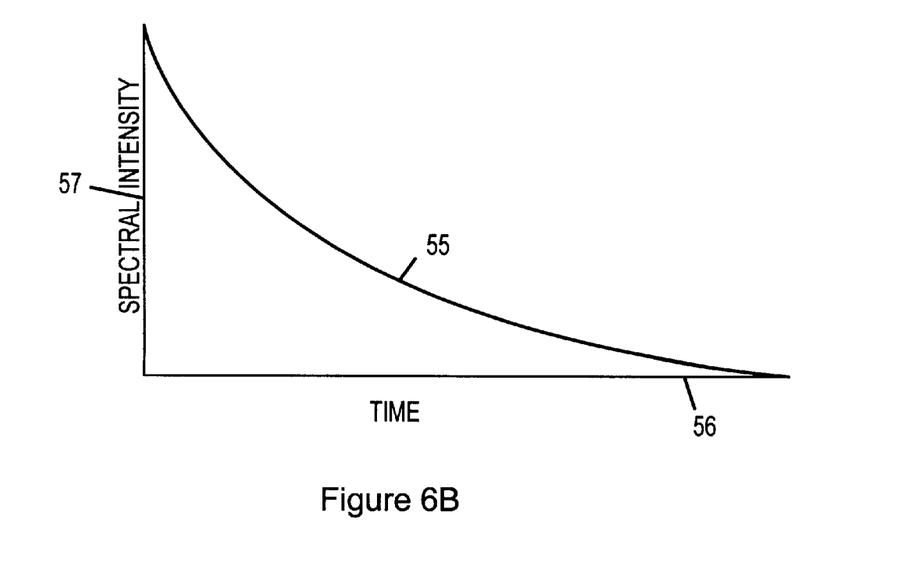

FIG. 6 illustrates one relevant method of data analysis and presentation that is particularly useful for pulsed excitation. The data can be analyzed by presenting it as a 3-dimensional plot such as shown in FIG. 6A. The data will have an axis 58 for spectral wavenumber, an axis 57 for absorbance, transmittance, or delta-absorbance, and a time axis 56. The signal at a given wavenumber may be presented as time series in a conventional 2-dimensional graph 55 indicated by FIG. 6B. FIG. 6B is a slice of FIG. 6A hence having the same time axis 56 and spectral intensity axis 57. The 3-dimensional plot of FIG. 6A may be thought of as a stack of 2-dimensional graphs, equivalent to FIG. 6B, one for each spectral element. Alternatively, the data may be conceptualized as a series of spectra, 51, 52, 53, and 54, one for each sampling time interval.

Figure 7A:
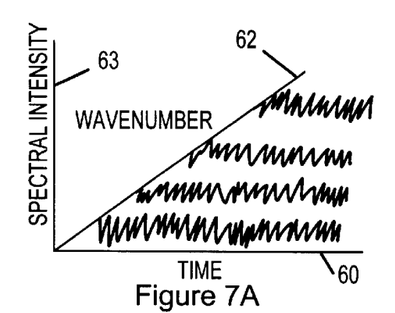
FIG. 7 is a diagram of a second preferred method of analyzing and presenting data in the frequency domain.
Figure 7B:
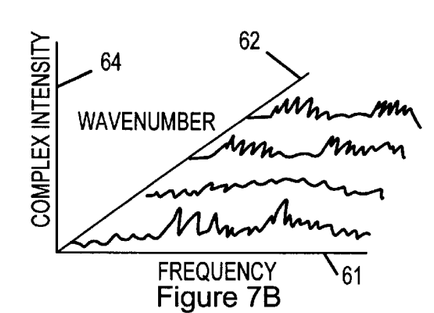
Figure 7C:
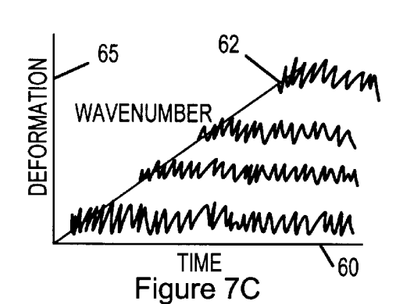
Figure 7D:
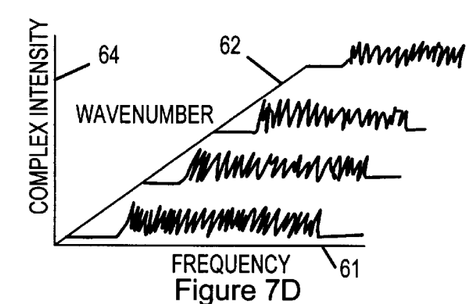
Figure 7E:
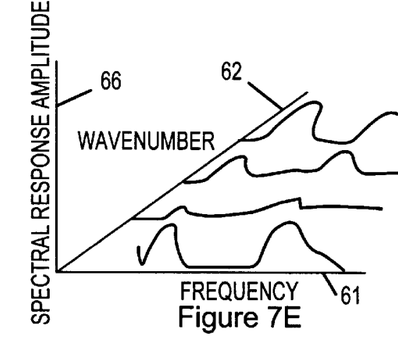
Figure 7F:
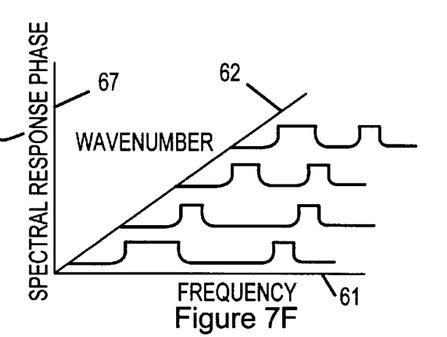

Another illustrative method of presenting the data is frequency domain plots. FIG. 7 shows the states of data during a sequence of signal processing involving Fourier transformation. The axes of FIG. 7 are time 60, frequency, 61, spectral wavenumber 62, spectral intensity 63, complex intensity 64, deformation 65, spectral response amplitude 66, and spectral response phase 67. The frequency domain data in FIG. 7B may be computed from the time domain response in FIG. 7A. The time axis of FIG. 6 is replaced by a frequency axis 61 indicating the response of the sample to each component frequency in the excitation waveform. The response amplitude shown in FIG. 7B, where the axis 64 indicates complex spectral intensity, may be normalized by dividing by the Fourier transform shown in FIG. 7D of the sample deformation shown in FIG. 7C. The axis 65 of FIG. 7C indicates deformation amplitude, while the axis 64 of 7D represents the complex intensity of deformation. One method to obtain the sample deformation motion is a reference measurement with the use of a totally absorbing sample mounted such that it blocks a portion of the spectrometer probe beam. Other methods of obtaining the deformation reference include measuring the output of transducer 24. Sample deformation data measured using a random phase waveform can be treated by Fourier transformation to produce a frequency domain representation as indicated by FIG. 7. The frequency domain sample response data of FIG. 7B is divided by the frequency domain deformation data shown in FIG. 7D to produce the normalized amplitude response shown in FIG. 7E. It is also appropriate to subtract the phase of the deformation waveform components from the phase of the response components to generate the corrected phase shown in FIG. 7F.

Additionally, it is possible to use multicomponent waveform signals that have any of several forms. One alternative is any waveform that has an integer number of sinusoidal components in which the integer is greater than two. The greater the number of frequencies, the greater the likelihood of hitting upon a frequency that generates a useful response in the sample. The ability of the present invention to generate and measure multiple frequency components at the same time amounts to multiplexing the measurements and is considered highly advantageous.

The principles, embodiments and modes of operation of the present invention have been set forth in the foregoing specification. The embodiments disclosed herein should be interpreted as illustrating the present invention and not as restricting it. The foregoing disclosure is not intended to limit the range of equivalent structure available to a person of ordinary skill in the art in any way, but rather to expand the range of equivalent structures in ways not previously considered. Numerous variations and changes can be made to the foregoing illustrative embodiments without departing from the scope and spirit of the present invention.

I claim:

1. A spectrometer for making multiplexed spectrorheological measurements, comprising:

a source of radiant energy;

a sample holder for holding a sample in the path of the radiant energy;

a force transfer device secured to the sample holder;

a frame member that secures the force transfer device so as to enable the force transfer device to transfer at least a deformation force to the sample;

a transducer also secured to the frame and acting on the force transfer device so as to impart a change in force to the sample based on a pseudorandom waveform signal;

a waveform generator for generating the waveform signal and transferring the waveform signal to the transducer, the waveform signal having three or more discrete frequency components;

a detector that receives radiant energy after it has interacted with the sample.

2. A spectrometer for making multiplexed spectrorheological measurements, comprising:

a source of radiant energy;

a sample holder for holding a sample in the path of the radiant energy;

a force transfer device secured to the sample holder;

a frame member that secures the force transfer device so as to enable the force transfer device to transfer at least a deformation force to the sample;

a transducer also secured to the frame and acting on the force transfer device so as to impart a change in force to the sample based on a pulsed waveform signal;

a waveform generator for generating the waveform signal and transferring the waveform signal to the transducer, the waveform signal having three or more discrete frequency components;

a detector that receives radiant energy after it has interacted with the sample.

3. A spectrometer for making multiplexed spectro-rheological measurements as claimed in claim 2, wherein the waveform signal contains all frequencies within the bandwidth of the waveform generator.

4. A spectrometer for making multiplexed spectro-rheological measurements as claimed in claim 2, wherein the waveform signal comprises a square wave.

5. A spectrometer for making multiplexed spectro-rheological measurements as claimed in claim 2, wherein the waveform signal comprises a sequence of pulses.

6. A spectrometer for making multiplexed spectro-rheological measurements, comprising:

a source of radiant energy;

a sample holder for holding a sample in the path of the radiant energy;

a force transfer device secured to the sample holder;

a frame member that secures the force transfer device so as to enable the force transfer device to transfer at least a deformation force to the sample;

a transducer also secured to the frame and acting on the force transfer device so as to impart a change in force to the sample based on a random waveform signal;

a waveform generator for generating the waveform signal and transferring the waveform signal to the transducer, the waveform signal having three or more discrete frequency components;

a detector that receives radiant energy after it has interacted with the sample.

7. A spectrometer for making multiplexed spectro-rheological measurements as claimed in claim 6, wherein the waveform signal contains all frequencies within the bandwidth of the waveform generator.

8. A spectrometer for making multiplexed spectro-rheological measurements as claimed in claim 6, wherein the discrete frequency components of the waveform have random amplitudes.

9. A spectrometer for making multiplexed spectro-rheological measurements as claimed in claim 6, wherein the discrete frequency components of the waveform have equal amplitudes.

10. A spectrometer for making multiplexed spectro-rheological measurements as claimed in claim 1, wherein the discrete frequency components of the waveform have equal amplitudes.

11. A spectrometer for making multiplexed spectro-rheological measurements as claimed in claim 1, wherein the waveform signal contains all frequencies within the bandwidth of the waveform generator.

12. A spectrometer for making multiplexed spectro-rheological measurements as claimed in claim 1, wherein the discrete frequency components of the waveform have random amplitudes.

* * * * *